United States Patent [19]
Eberle et al.

[11] Patent Number: 5,167,233
[45] Date of Patent: Dec. 1, 1992

[54] DILATING AND IMAGING APPARATUS

[75] Inventors: Michael J. Eberle, Citrus Heights, Calif.; John M. Hodgson, Shaker Heights, Ohio

[73] Assignee: Endosonics Corporation, Rancho Cordova, Calif.

[21] Appl. No.: 638,192

[22] Filed: Jan. 7, 1991

[51] Int. Cl.⁵ .............................................. A61B 10/00
[52] U.S. Cl. ........................... 128/662.06; 128/660.03
[58] Field of Search .................... 128/660.03, 662.06; 606/149, 159; 604/99–103

[56] References Cited
U.S. PATENT DOCUMENTS

| | | | |
|---|---|---|---|
| 4,665,925 | 5/1987 | Millar | 128/662.06 X |
| 4,794,931 | 1/1989 | Yock | 128/662.06 X |
| 4,841,977 | 6/1989 | Griffith et al. | 128/662.06 |
| 4,917,097 | 4/1990 | Proudian et al. | 128/662.06 |
| 4,951,677 | 8/1990 | Crowley et al. | 128/662.06 |
| 5,046,503 | 9/1991 | Schneiderman | 128/662.06 X |

Primary Examiner—Francis Jaworski
Attorney, Agent, or Firm—Leydig, Voit & Mayer

[57] ABSTRACT

A dilating and imaging apparatus for attaching to and receiving pressurized fluid from a distal end of a catheter. The apparatus includes an inflatable balloon and an imaging device positioned behind an expandable portion of the balloon and upstream of the flow of pressurized fluid into the balloon so as to enable the balloon to deflate and achieve a smaller diameter than that of the imaging device, thus enabling the apparatus to enter a stenosis having a smaller diameter than the imaging device. In one embodiment of the invention, the imaging device can be maneuvered within the balloon while the balloon is inflated and dilating the stenosis.

15 Claims, 7 Drawing Sheets

DILATING AND IMAGING APPARATUS

FIELD OF THE INVENTION

The present invention relates generally to percutaneous transluminal coronary angioplasty (PTCA) and ultrasonic imaging, and more particularly to a single apparatus having both capabilities.

BACKGROUND OF THE INVENTION

Intravascular balloon catheters that include ultrasonic imaging devices provide an effective alternative to coronary bypass surgery. Transluminal angioplasty surgery utilizes an elongated, flexible catheter having an inflatable balloon at its distal end that is inserted at an appropriate position in a vascular system of a patient. After the catheter is inserted into the vascular system, its balloon is routed to a stenosis. Once the balloon is properly positioned relative to the stenotic lesion, it is inflated with fluid under relatively high pressure. As the balloon expands, it dilates the stenosis, thus allowing blood to flow more freely.

Conventional methods of locating the exact position of a stenosis typically consist of injecting a contrast compound, such as a substance that is opaque to radiation, into the patient's bloodstream so that fluoroscopy can be used to enable the physician to view the flow of blood. To treat the stenosis, the physician first inserts a guide wire into the occluded vessel. After the guide wire has reached the stenosis or the occluded vessel, a tubular catheter having a lumen for the guide wire is pushed along the guide wire and guided by the guide wire until fluoroscopy reveals that the balloon is located within the stenosis. The balloon is then inflated to dilate the stenosis. When the balloon is deflated and removed from the vessel, blood is able to flow more freely through the enlarged stenosis.

While fluoroscopy enables the physician to locate the position of the stenosis, it fails to provide the physician with detailed, real-time images of the anatomy causing the stenosis during and after the dilation procedure. The limitations of fluoroscopy has lead to attempts to improve upon imaging of the stenosis being treated. One such method uses two catheters, wherein one catheter has an ultrasonic imaging device at its distal end and the other catheter has the inflatable balloon at its distal end. In practicing this method, the balloon catheter is first inserted into the vessel along the guide wire, positioned within the stenosis, and the balloon is inflated to dilate the stenosis. The balloon catheter is then removed and the imaging catheter is inserted to enable the physician to examine the stenosis and determine if further treatment is needed. Obviously, it would be more desirable to have only one catheter that has both dilating and imaging capabilities, thereby eliminating the catheter exchange procedure and further providing realtime images of the dilating procedure.

One example of a catheter having both dilating and imaging capabilities is disclosed in U.S. Pat. No. 4,841,977 to Griffith et al. which positions the imaging device inside the inflatable balloon. The positioning of the imaging device inside the balloon instead of behind the balloon appears to be necessary to prevent the imaging device from interfering with the flow of pressurized fluid into the balloon. While this design provides a catheter having both dilating and imaging capabilities, the low profile of balloon when deflated is limited to a diameter of the imaging device, thus preventing the deflated balloon from entering very narrow stenoses and limiting the accessibility of the catheter to larger diameter stenoses.

U.S. Pat. No. 4,917,097 to Proudian et al. also discloses a catheter having both dilating and imaging capabilities, wherein the imaging device is positioned at a distal end of the balloon. Similarly to Griffith et al., the capability of the Proudian balloon to enter very small diameter stenoses is limited by the relatively large diameter of the imaging device. In order to optimize these types of catheters, it is important for the balloon to be able to enter even the very narrow stenoses.

Another limitation of balloon catheters including imaging devices is the highly directional characteristic of imaging devices. Imaging devices typically include an imaging array that enables the device only to image an integral (or "slice") of the stenosis immediately adjacent to the periphery of the array. Therefore, the entire balloon catheter must be moved in order for the physician to examine additional integrals of the stenosis.

SUMMARY OF THE INVENTION

In view of the foregoing, it is a primary object of the present invention to provide a dilating assembly capable of both dilating a stenosis of a blood vessel with an inflatable balloon and imaging the stenosis with an ultrasonic imaging device, wherein the inclusion of the imaging device on the catheter does not affect the ability of the balloon to achieve a very low profile and be able to enter very narrow stenoses.

Another object of the present invention is to provide a dilating assembly capable of both achieving a low profile of very small diameter and dilating a stenosis while simultaneously imaging the entire portion of the stenosis being dilated.

An additional object of the present invention is to provide an imaging catheter capable of providing a high quality image.

In keeping with the foregoing objects, the invention generally provides a dilating and imaging apparatus for attaching to and receiving pressurized fluid from a distal end of a catheter. The apparatus includes an inflatable balloon and an imaging device positioned behind an expandable portion of the balloon and upstream of the flow of pressurized fluid into the balloon so as to enable the balloon to deflate and achieve a smaller diameter than that of the imaging device, this aspect enabling the apparatus to enter a stenosis having a smaller diameter than the imaging device.

In one embodiment of the invention, the imaging device can be maneuvered within the balloon while the balloon is inflated and dilating the stenosis.

Other objects and advantages of the invention will become apparent as the following description proceeds taken in conjunction with the accompanying drawings.

BRIEF DESCRIPTION OF THE DRAWINGS

FIG. 2b is an enlarged cross-sectional view of an imaging device within an inflatable balloon of the dilating apparatus shown FIG. 2a;

FIG. 3b is an enlarged cross-sectional view of an imaging device within an inflatable balloon of the dilating apparatus shown in FIG. 3a;

FIG. 4b is an enlarged cross-sectional view of an imaging device within an inflatable balloon of the dilating apparatus shown in FIG. 4a;

While the invention will be described in connection with preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENTS

Figure 1A:
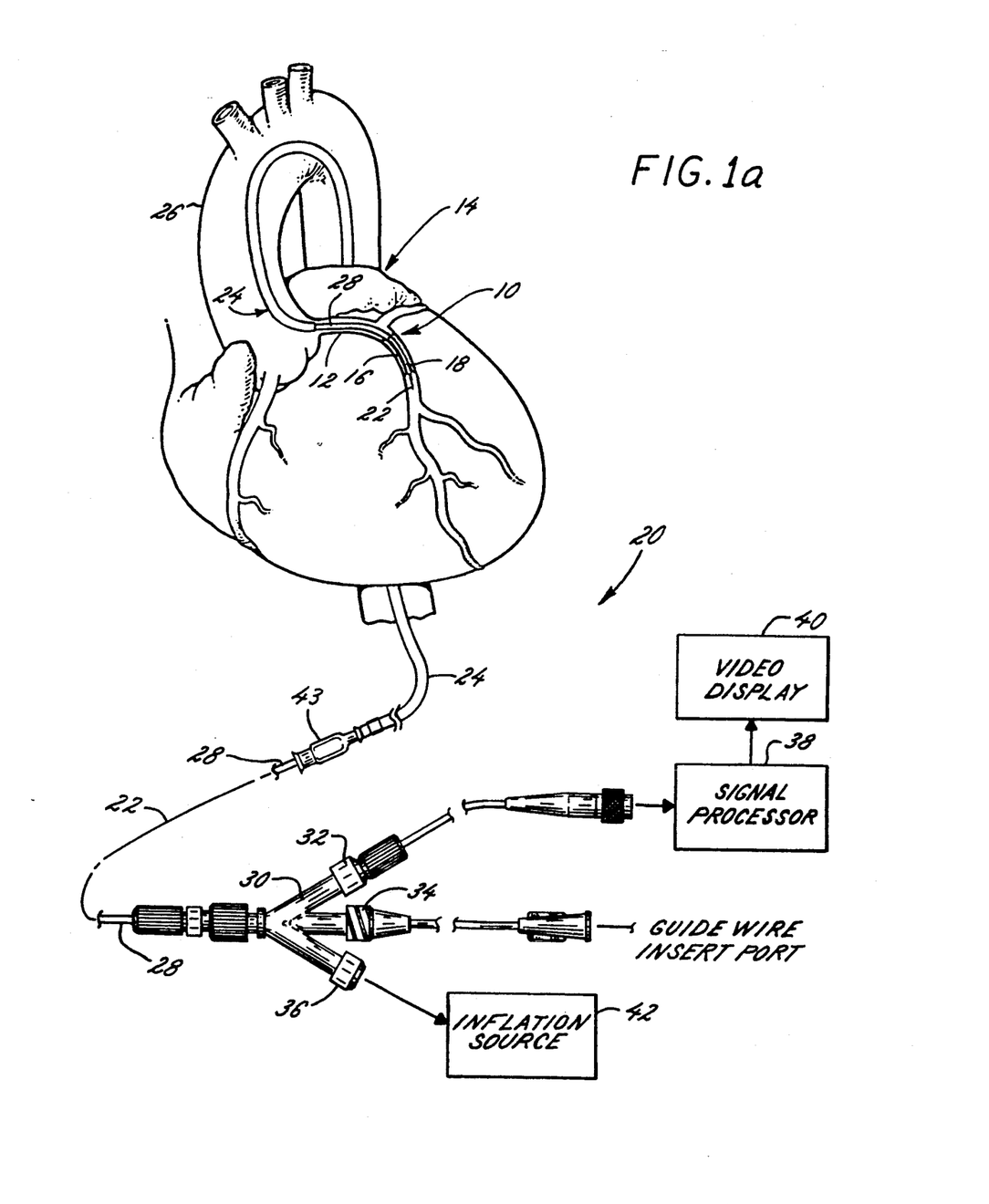
FIG. 1a is a schematic illustration of a catheter assembly according to the invention utilized for an angioplasty procedure in a coronary artery of a heart.

Turning now to the drawings, FIG. 1a illustrates a dilating and imaging apparatus 10 according to the present invention as it is being utilized in a coronary artery 12 of a heart 14. The coronary artery 12 contains a buildup of fatty material or plaque 16 that is causing the coronary artery 12 to become occluded or have a stenosis.

The occluded section or stenosis 16 of the artery 12 may be treated by inserting a balloon 18 of the dilating apparatus 10, in a low profile or deflated state, into the artery 12 by using a catheter assembly 20. As illustrated in FIG. 1a, the catheter assembly 20 is a three-part assembly, having a guide wire 22, a guide catheter 24 for threading through large arteries such as the aorta 26, and a smaller diameter catheter 28 that fits inside the guide catheter 24. The catheter assembly 20 includes a tri-arm adapter 30 having a signal processor port 32, a guide wire insert port 34, and an inflation port 36 that is in communication with a fluid lumen in the catheter 28. The tri-arm adaptor 30 enables a signal processor 38 (that is linked to a video display 40), a guide wire 22, and an inflation source 42 all to be interconnected within the smaller catheter 28 and to communicate with the dilating and imaging apparatus 10. The smaller catheter 28 is inserted into the larger guide catheter 24 by means of a luer lock connector or angioplasty manifold 43 before entering the heart 14. The smaller diameter catheter 28 and the larger diameter catheter 24 may be made of a suitable, flexible material such as polyolefin or polyvinylchloride.

After a surgeon directs the guide wire 22 and then the guide catheter 24 through a large artery leading into the aorta 26, the smaller diameter catheter 28 is inserted. At the beginning of the coronary artery 26 that is partially occluded by the stenosis 16, the guide wire 22 is first extended into the artery 12, followed by the smaller catheter 28, which includes the balloon 18 on a distal end of the catheter 28.

In accordance with an important aspect of the present invention, a single dilating and imaging apparatus is provided that is capable of achieving a low profile having a smaller diameter than that of an imaging device located within a proximal sleeve of the balloon. Means are provided for communicating the flow of pressurized fluid past the imaging device before entering an expandable portion of the balloon. In the illustrated embodiment of FIG. 1b, an imaging device 44 is positioned within the proximal sleeve 46 of the balloon 18 in order to enable the balloon 18 to achieve a low profile having a smaller diameter than that of the imaging device 44. This is possible because the imaging device 44 is positioned within the proximal sleeve 46 that is behind an expandable portion of the balloon 18. The expandable portion of the balloon 18 is that portion of the balloon 18 between the proximal sleeve 46 and the distal sleeve 52.

Figure 1B:
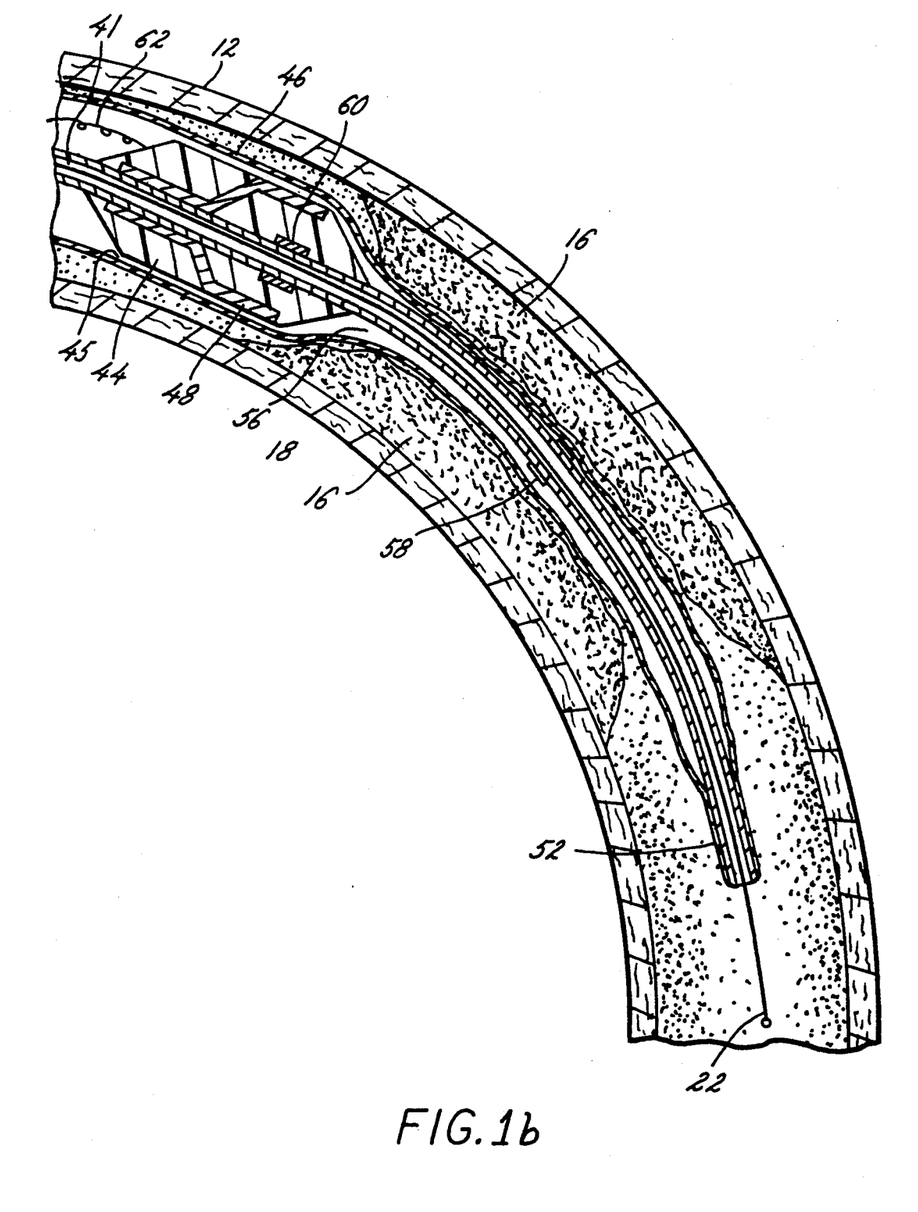
FIG. 1b is an enlarged cross-sectional view of a distal end of a dilating apparatus according to the invention positioned within a stenosis as shown in FIG. 1b.

The imaging device 44 includes a central bore 41 for maintaining a first lumen 39 through the imaging device 44 and into the balloon 18. The central bore 41 enables the guide wire 22, which is passed through a tubing 50, to pass through the center of the imaging device 44. FIG. 1b shows how the deflated balloon 18 is able to follow the guide wire 22 and enter a stenosis 16 having a smaller diameter than the imaging device 44 because the imaging device 44 is positioned in the proximal sleeve 46 of the balloon 18.

The balloon 18 enters the stenosis or occluded artery 16 in a low profile or deflated state. Once the balloon 18 is properly positioned within the stenosis 16, pressurized fluid communicated to the interior of the balloon 18 via the catheter 28 causes the balloon 18 to inflate and dilate the stenosis 16. After the stenosis 16 has been dilated by the inflated balloon 18, the balloon is deflated by withdrawing the pressurized fluid. The proximal sleeve 46 of the balloon 18, which contains the imaging device 44, then may be positioned inside the dilated stenosis 16 by further inserting the catheter 28 into the artery 12. An imaging array 48 located within the imaging device 44 is highly directional and, therefore, the imaging device 44 must be able to enter the dilated stenosis in order to generate a complete image of the dilated stenosis 16.

Figure 2A:
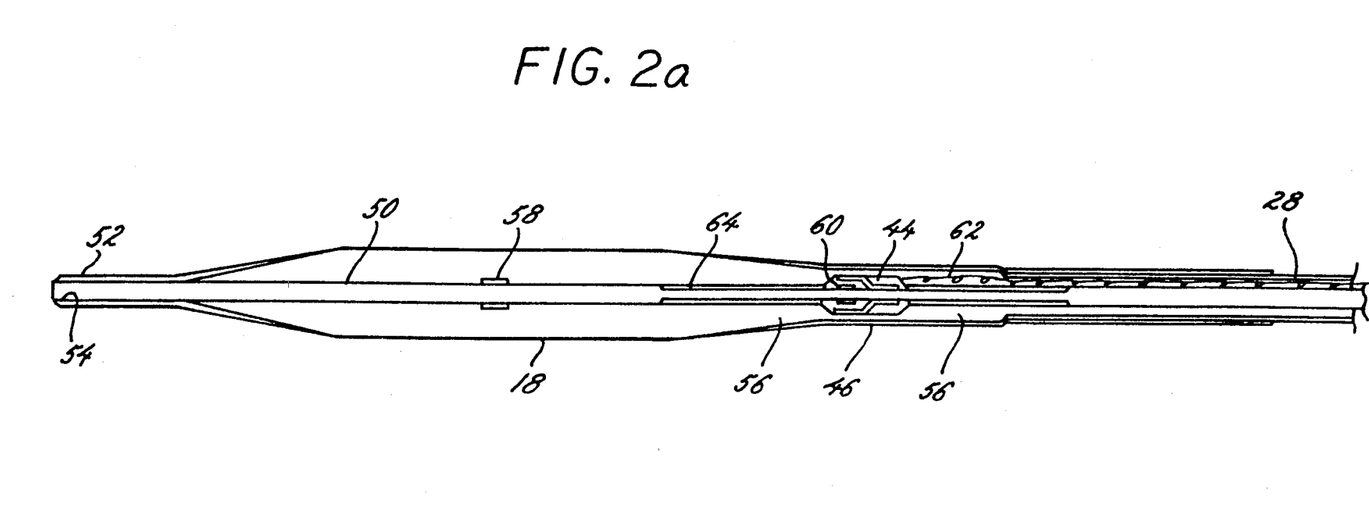
FIG. 2a is cross-sectional view of the distal end of the dilating apparatus taken along a longitudinal axis of the catheter.
Figure 2B:
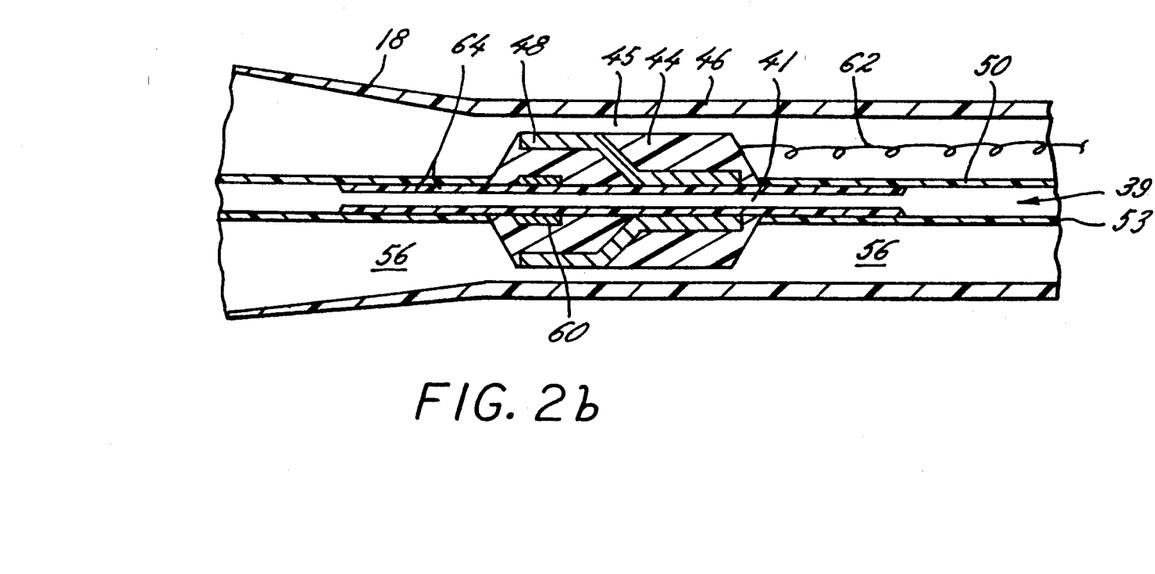

FIGS. 2a and 2b are cross-sections of one embodiment of the present invention. FIG. 2b is an enlarged cross-sectional view of the proximal sleeve 46 and the imaging device 44 shown in FIG. 2a. The tubing 50 having a first lumen 39 extends through the interior of the balloon 18. The tubing 50 runs parallel with a longitudinal axis of the catheter 28. A distal sleeve 52 of the balloon 18 is hermetically sealed, or joined, to a distal end 54 of the tubing 50, and the proximal sleeve 46 of the balloon 18 is hermetically sealed, or joined, to an outer surface of the smaller diameter catheter 28, thereby sealing off the interior of the balloon 18 from the external environment. Likewise, a proximal end 53 of the tubing 50 is connected to a distal end of a guide wire lumen (see FIGS. 7a–c) of the catheter 28. The balloon 18 may be secured to the tubing 50 with a sealant or by heating the balloon 18 in order to constrict the distal sleeve 52 and the proximal sleeve 46 around the tubing 50 and the catheter 28, respectively.

The balloon 18 is coaxial to and encompasses the tubing 50 which creates a second lumen 56 between an inner wall of the balloon 18 and an outer surface of the tubing 50. Means for communicating the flow of pressurized fluid past the imaging device 44 are provided by an annular passageway 45 within the second lumen 56. The annular passageway 45 is formed between a peripheral surface of the imaging device 44 and an inner wall of the proximal sleeve 46 such that the pressurized fluid is in communication with the interior of the balloon 18. The imaging device 44 is in direct contact with the pressurized fluid, and therefore, should be insulated from the pressurized fluid by a protective sealant. One type of protective sealant that may be used is a thin coating of parylene polymer. Parylene polymer is a product trade name and manufactured by Union Carbide Corporation.

A fluoroscopically visible cylindrical marker band 58 is secured around the tubing 50 at a location within the balloon 18. Another marker band 60 is located within the imaging device 44. The marker bands 58 and 60 enable the position of the balloon 18 and the imaging array 44 to be monitored as the catheter 28 is inserted into the vascular system of the patient. Additional marker bands may be secured to the apparatus 10 in order to monitor specific sections of the apparatus 10. For example, an additional marker band (not shown) may be secured to the distal end of the tubing 50 in order to monitor the position of the distal sleeve 52. The marker bands may be fabricated of gold or other suitable dense metal. The marker bands typically have a wall thickness on the order of 0.003 inches and an internal diameter corresponding to the surface diameter of the tubing 50 to which the marker bands are to be mounted.

A micro-cable 62, that extends through the second lumen 56 back to the proximal end of the catheter 28, interlinks electronics of the imaging device 44 to the signal processor 38 (FIG. 1). The micro-cable 62 is about 0.017 inches in diameter and has a number of individual insulated conductors.

Technical details of the electronics of the imaging device 44 are disclosed in U.S. Pat. No. 4,917,097 to Proudian et al. The signal processor 38 is connected to a video display 40 that displays an image of the stenosis 16 as detected by the imaging array 48.

The imaging device 44 is situated within the proximal sleeve 46 by mounting means. The mounting means may include securing the imaging device 44 directly to the tubing 50. For added strength, however, the tubing 50 is spliced at a location within the proximal sleeve 46 and a tubing coupling 64, to which the imaging device 44 is secured, is inserted into opposing ends of the slice. The tubing coupling 64 is more sturdy than the tubing 50 and provides a stronger mounting for the imaging device 44. The tubing coupling 64 can be constructed of a sturdy material such as polyamide.

Figure 3A:
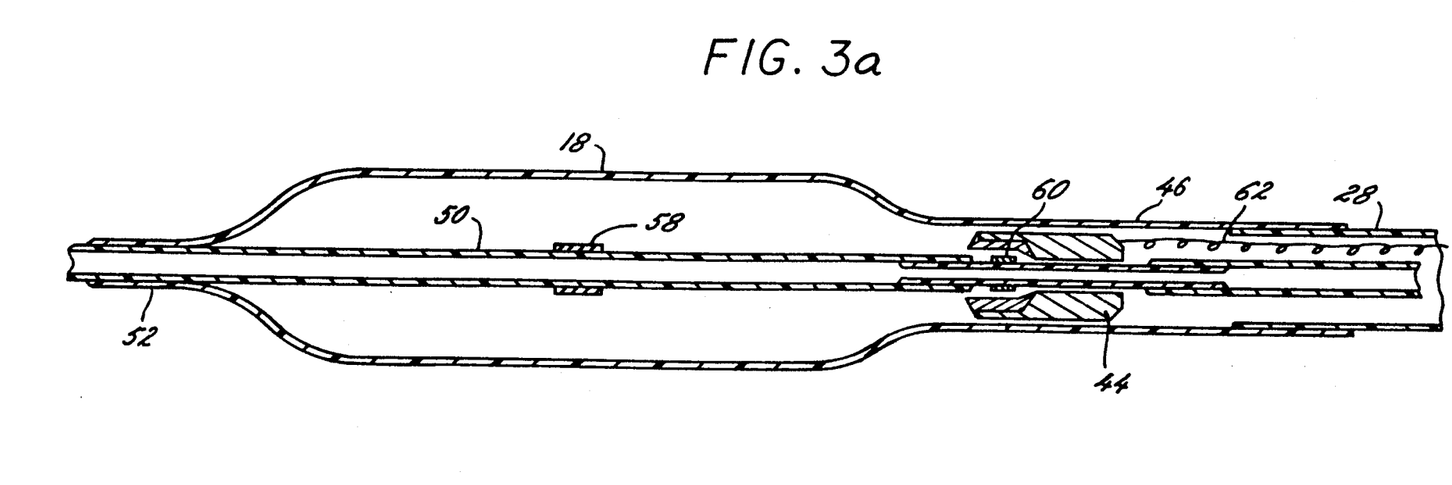
FIG. 3a is a cross-sectional view of a second embodiment of the distal end of the dilating apparatus taken along the longitudinal axis of the catheter.
Figure 3B:
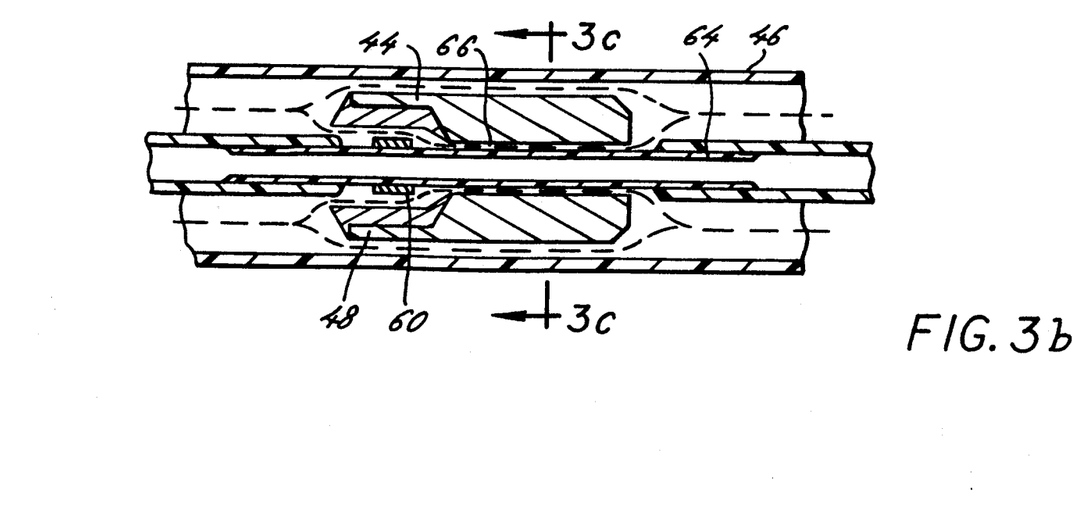
Figure 3C:
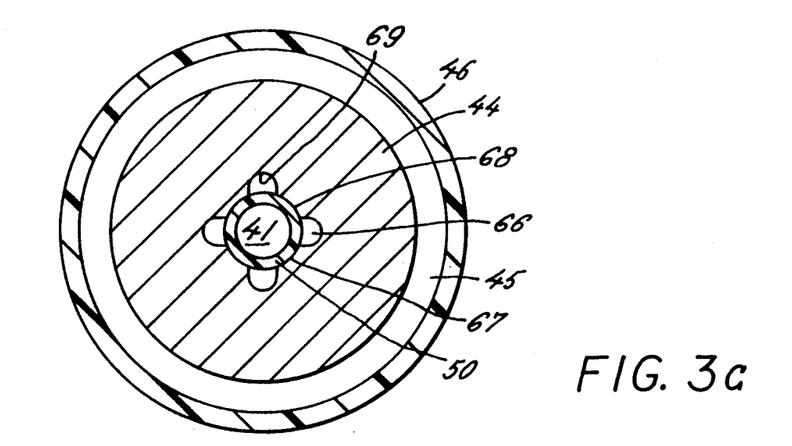
FIG. 3c is a cross-sectional view of the imaging device taken along line 3c—3c of FIG. 3b.

FIGS. 3a–3c illustrate another embodiment of the present invention, wherein another communicating means and mounting means are provided. FIG. 3a shows a cross-sectional view of the apparatus 10 and FIG. 3b shows an enlarged view of the proximal sleeve 46 which contains the imaging device 44. The communicating means include both an annular passageway 45 and a plurality of central passageways 66. The plurality of central passageways 66 are located between an outer surface 67 of the tubing 50 and an inner surface 69 of the central bore 41 (FIG. 3c).

FIG. 3c shows a cross-sectional view of the imaging device 44 shown in and taken along line 3c—3c of FIG. 3b. The plurality of central passageways 66 run parallel with the tubing 50 and are positioned between the inner surface 69 of the central bore 41 and the outer surface 67 of the tubing 50. The mounting means include mounting segments 68 of the central bore 41 which are secured to portions of the outer surface of the tubing 50. This embodiment increases the flow rate of the pressurized fluid to and from the balloon 18, but it is more difficult and costly to produce.

Figure 4A:
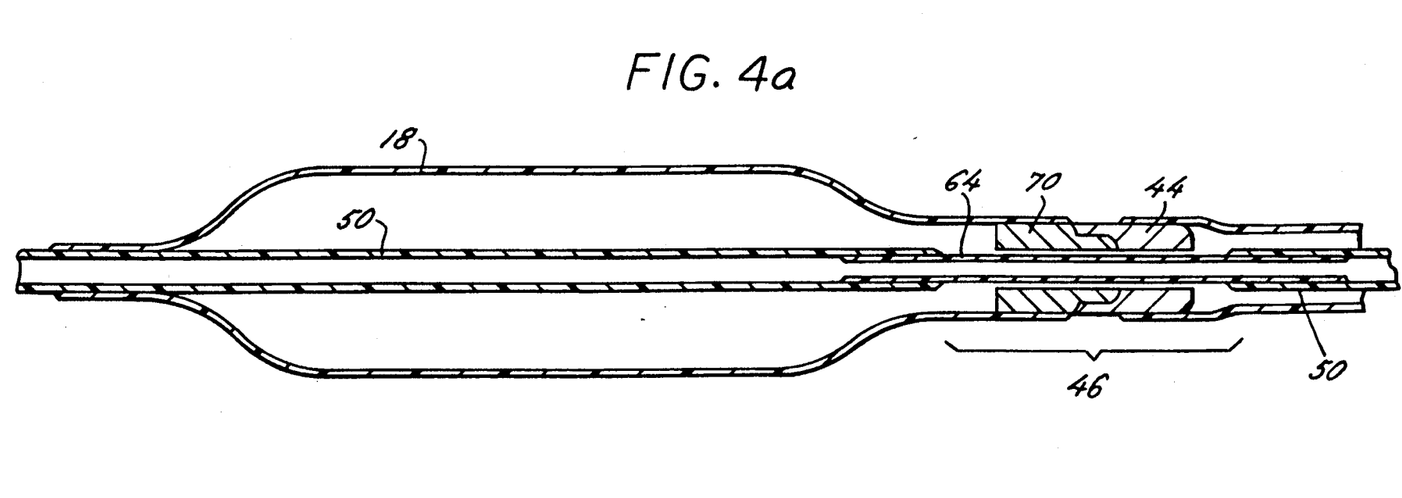
FIG. 4a is a cross-sectional view of a third embodiment of the distal end of the dilating apparatus taken along the longitudinal axis of the catheter.
Figure 4B:
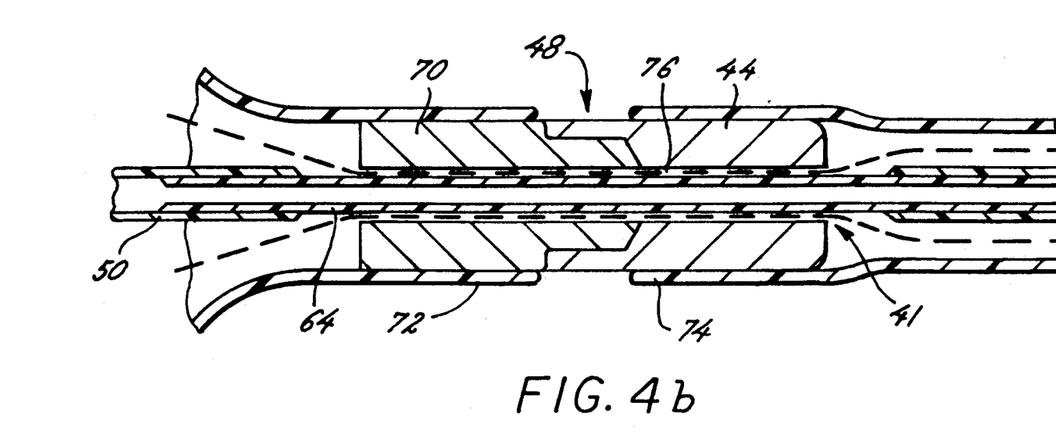

FIGS. 4a and 4b illustrate another embodiment of the invention wherein the imaging array 48 is exposed directly to blood in the artery. The feature enables the apparatus 10 to provide a high quality image because there is no attenuation or reflection (echo) resulting from a barrier between the imaging array 48 and the inner walls of the artery 12, except for the blood which provides a medium for ultrasonic waves generated by the imaging array 48. Furthermore, this configuration also positions the imaging device 44 behind the expandable portion of the balloon 18.

The imaging device 44 includes a carrier extension 70 that is attached to the imaging device 44. The carrier extension may be formed from a rigid plastic, epoxy, metal or suitable material. The proximal sleeve is spliced to create an anterior end 72 and a posterior end 74. Mounting means are provided by securing the carrier extension 70 to the anterior end 72 and securing the posterior end 74 to the imaging device 44. Communicating means are provided by a gap 76 between the inner wall 47 of the central bore 41 and the outer surface of the tubing 50.

Similarly to the embodiment shown in FIGS. 2a and 3a, a tubing coupling 64 may be used to provide a section of the tubing 50 that is smaller in diameter and has thinner walls. This embodiment allows for the gap 76 to exist between the outer surface of the tubing coupling 64 and the inner wall 47 of the central bore 41.

Figure 5:
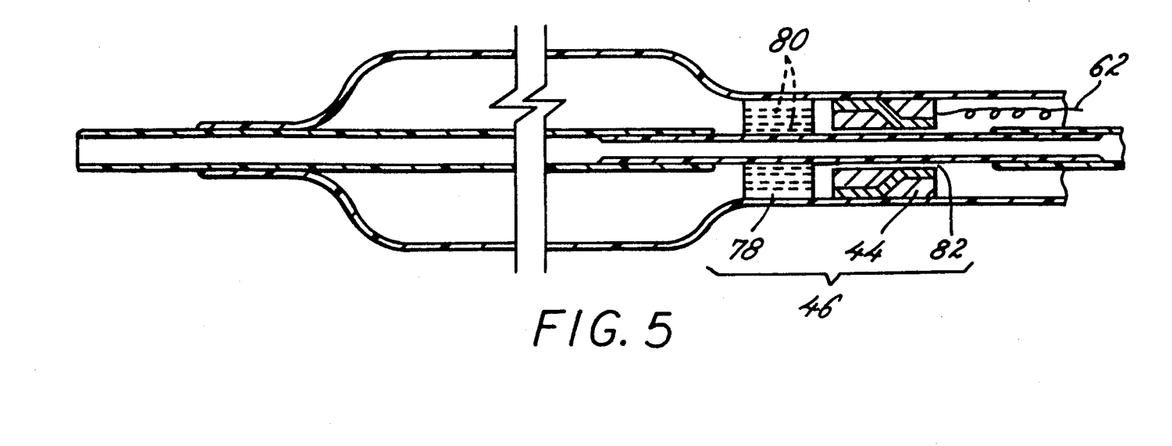
FIG. 5 is a cross-sectional view of a fourth embodiment of the distal end of the dilating apparatus taken along the longitudinal axis of the catheter.

FIG. 5 illustrates another embodiment of the present invention wherein the proximal sleeve 46 includes a lumen attachment 78 located between the imaging device 44 and the expandable portion of the balloon 18. The lumen attachment is a ring-shaped spacer that serves to position the proximal sleeve 46 at a radially spaced position from the tubing 50. The ring-shaped spacer is made of any suitable rigid material. An inner wall of the attachment 78 is mounted to the outer surface of the tubing coupling 64, and an outer surface of the attachment 78 is mounted to the inner wall of the proximal sleeve 46. The lumen attachment 78 also includes flow channels 80 that enable the pressurized fluid to pass through the lumen attachment 80.

The communicating means include a gap 82 similar to gap 76 of FIG. 4a. The flow channels 80 in combination with the gap 82 provide means for communicating the pressurized fluid to the balloon 18. Means for mounting the imaging device 44 are provided by securing the outer periphery of the imaging device 44 to the inner wall of the proximal sleeve 46. This embodiment provides additional mechanical support to the proximal sleeve 46. The prior embodiment illustrated in FIG. 2a places a great deal of operational forces on the proximal sleeve 46. The lumen attachment 78 in this embodiment provides additional support to the proximal sleeve 46 in order to lessen the operational forces on the proximal sleeve 46.

Figures 6A, 6B, 6C:
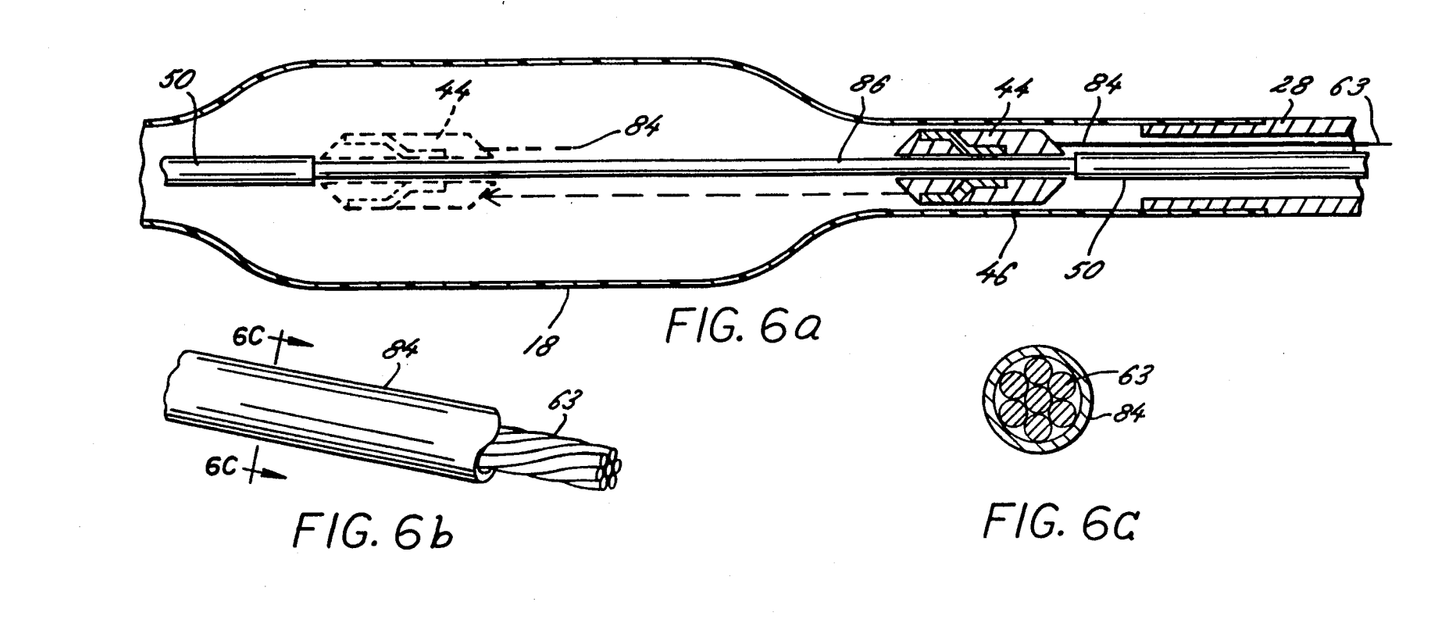
FIG. 6a is a cross-sectional view of a fifth embodiment of the distal end of the dilating apparatus taken along the longitudinal axis of the catheter.
FIG. 6b is an enlarged view of a push wire within the dilating apparatus shown in FIG. 6a wherein a microcable is contained within the push wire.
FIG. 6c is a cross-sectional view of the push wire taken along line 6c—6c of FIG. 6b.

FIG. 6a illustrates another important aspect of the present invention, wherein the imaging device 44 is slidably mounted to the tubing 50 so as to enable the imaging device 44 to generate a complete image of the stenosis 16 while the inflated balloon 18 simultaneously dilates the stenosis 16 in this embodiment. A push wire 84 is attached to the imaging device 44 and extends back through the second lumen 56 to the proximal end of the catheter 28. As illustrated in FIGS. 6b and 6c, the push wire 84 is a flexible hypotube (thin-walled tube) wherein a micro-cable 63 is located inside the push wire 84. The diameter of the push wire 84 is approximately 0.014 inches. The push wire 84 enables a surgeon to remotely maneuver the imaging device 44 within the balloon 18 while the balloon 18 is inflated. The surgeon can image the entire portion of the stenosis 16 being dilated by the inflated balloon 18 by sliding the imaging device 44 along the entire length of the tubing 50 that is located within the expandable portion of the balloon 18.

A portion of the tubing 50 that is located within the proximal sleeve 46 and the expandable portion of the balloon 18 is preferably be replaced with a sturdier micro-tube 86 in order to enable the imaging device 44 to slide more easily within the balloon 18. The micro-tube 86 is similar to the tubing coupling 64 because it is inserted in opposing ends of a splice in the tubing 50. The micro-tube 86 may also be made from polyamide.

In practicing this slidable embodiment of the invention, the imaging device 44 is initially positioned within the proximal sleeve 46 when the balloon 18 is deflated and being inserted into the stenosis 16. Positioning the device 44 within the proximal sleeve 46 enables the balloon 18 to achieve a low profile that is not restricted by the diameter of the imaging device 44. After the balloon 18 is inflated with pressurized fluid, the surgeon then uses the push wire 84 to push the imaging device out of the proximal sleeve 46 and into the expandable portion of the balloon 18. By sliding the imaging device 44 along the micro-tube 86, the surgeon is able to image all sections of the stenosis 16 which are being dilated by the inflated balloon.

After sliding the imaging device 44 along the microtube 86 and imaging all sections of the stenosis 16 being dilated by the inflated balloon, the surgeon may then deflate the balloon 18 and image the stenosis 16 in order to determine whether the stenosis 16 maintains a dilated form after the balloon 18 is removed. In practicing this procedure, the imaging device 44 is first maneuvered back into the proximal sleeve 46 before deflating the balloon 18. After the balloon 18 is deflated, the stenosis 16 is imaged by inserting the proximal sleeve 46, which contains the imaging device 44, further into the stenosis 16.

Figure 7A:
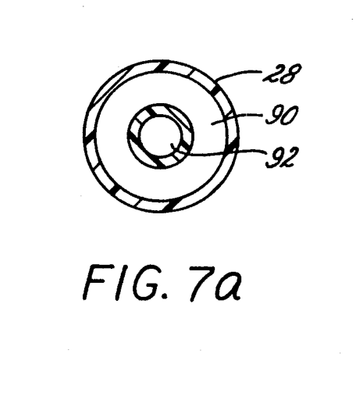
FIGS. 7a–c are cross-sectional views of possible embodiments of the catheter that is connected to the invention, wherein lumens within the catheter are arranged differently in each embodiment.
Figure 7B:
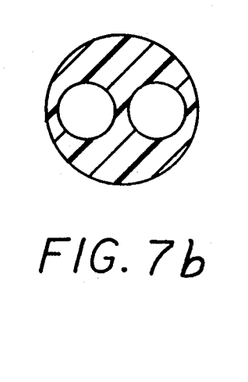
Figure 7C:
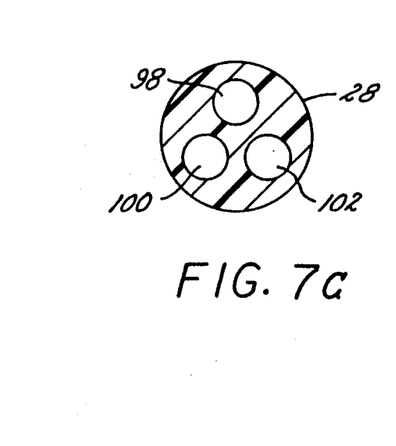

The apparatus of the invention may be secured to catheters having various lumen configurations. For example, FIG. 7a illustrates a coaxial lumen arrangement wherein the pressurized fluid, micro-cable 62 (or push wire 84) may pass through the outer lumen 90 and the guide wire 22 may pass through the inner lumen 92. As an alternative, FIG. 7b illustrates a side-by-side lumen arrangement wherein the guide wire 22 may pass through lumen 94, and the pressurized fluid and micro-cable 62 may pass through lumen 96. Illustrating another possible embodiment, FIG. 7c discloses a tri-lumen arrangement wherein the guide wire 22 may pass through lumen 98, the pressurized fluid may pass through lumen 100, and the micro-cable 62 (or push wire 84) may pass through lumen 102. For each of these illustrated embodiments, the apparatus of the present invention is simply secured to the distal end of the catheter in a conventional manner so that the guide wire 22, pressurized fluid, and micro-cable 62 (or push wire 84) communicate correctly with the apparatus. Of course, these illustrated lumens are only exemplary of the different catheters that may be used with this invention and are not intended to limit the invention to only those catheters illustrated herein.

We claim as our invention:

1. A dilating and imaging apparatus secured to a catheter, the catheter having distal and proximal ends, a fluid lumen, and a guide wire lumen receiving a guide wire, the apparatus comprising:

a tubing having distal and proximal ends and a first lumen in communication with the guide wire lumen of the catheter, wherein the proximal end of the tubing is connected to the distal end of the catheter;

an inflatable balloon having distal and proximal sleeves, the balloon being coaxial to and encompassing the tubing so as to form a second lumen between an outer surface of the tubing and an inner surface of the proximal sleeve, the distal sleeve being sealed to the distal end of the tubing, and the proximal sleeve joining to the distal end of the catheter so that the pressurized fluid from the fluid lumen of the catheter may flow to the interior of the balloon via the second lumen and inflate the balloon;

an imaging device having a central bore for permitting the guide wire to pass through the imaging device and into the tubing;

means for mounting the imaging device within the proximal sleeve of the balloon so that the imaging device is positioned behind the expandable portion of the balloon and upstream of the flow of pressurized fluid into the balloon so as to enable the balloon to achieve a low profile having a diameter smaller than that of the imaging device; and means for communicating the flow of pressurized fluid past the imaging device before entering the expandable portion of the balloon.

2. The apparatus as set forth in claim 1, wherein the guide wire and fluid lumen of the catheter are coaxial.

3. The apparatus as set forth in claim 1, wherein the guide wire and fluid lumen of the catheter are in a side-by-side arrangement.

4. The apparatus as set forth in claim 1, wherein the mounting means include mounting the imaging device to the tubing and the communicating means include an annular passageway for the pressurized fluid to flow between a peripheral surface of the imaging device and an inner wall of the proximal sleeve such that the pressurized fluid is in contact with the imaging device.

5. The apparatus as set forth in claim 4, wherein the communicating means include a plurality of central passageways enabling the pressurized fluid to flow between an inner wall of the central bore and an outer surface of the tubing so that the pressurized fluid is able to pass through the device, and the mounting means further include mounting segments on the inner wall of the central bore which are secured to the outer surface of the tubing.

6. The apparatus as set forth in claim 1 in which the proximal sleeve of the balloon has a discontinuity exposing an imaging array of the imaging device to direct contact with blood external to the apparatus in order to increase imaging sensitivity of the array, the mounting means include securing the device to the inner wall of the proximal sleeve, and the communicating means include a gap between an inner wall of the central bore and an outer surface of the tubing that enables the pressurized fluid to pass through the imaging device.

7. The apparatus as set forth in claim 6, further comprising:
a carrier extension on the imaging device, wherein an anterior end of the discontinuity mounts to the carrier extension and a posterior end of the discontinuity mounts to the imaging device.

8. The apparatus as set forth in claim 1, further comprising:
a lumen attachment for securing a portion of the proximal sleeve of the balloon at a radially spaced position from the tubing, the lumen attachment being positioned between the imaging device and the expandable portion of the balloon, and the lumen attachment including flow channels enabling the pressurized fluid to pass through the lumen attachment from the second lumen to the interior of the balloon.

9. The apparatus as set forth in claim 8, wherein the mounting means include securing a peripheral surface of the imaging device to an inner wall of the proximal sleeve of the balloon, and the communicating means include a gap between an inner wall of the central bore and an outer surface of the tubing that enables the pressurized fluid to pass through the imaging device.

10. A dilating and imaging apparatus secured to a catheter, the catheter having distal and proximal ends, a fluid lumen, and a guide wire lumen for receiving a guide wire,, the apparatus comprising:
a tubing having distal and proximal ends and a first lumen for receiving the guide wire communicated to the first lumen from the guide wire lumen of the catheter, wherein the proximal end of the tubing is connected to a distal end of the guide wire lumen of the catheter;
an inflatable balloon having distal and proximal sleeves, the balloon being coaxial to and encompassing the tubing so as to form a second lumen between an outer surface of the tubing and an inner surface of the proximal sleeve, the distal sleeve joining to the distal end of the tubing, and the proximal sleeve joining to the distal end of the catheter so that the pressurized fluid from the fluid lumen of the catheter may flow to the interior of the balloon via the second lumen and inflate the balloon;
an imaging device slidably mounted on the tubing for sliding the device along the tubing from a position within the proximal sleeve to a position within the expandable portion of the balloon so as to enable the balloon to achieve a low profile having a diameter smaller than that of the imaging device;
a push wire attached to the imaging device that extends through the second lumen and back to the proximal end of the catheter in order to remotely control the sliding of the device along the tubing; and
means for communicating the flow of pressurized fluid past the imaging device when it is positioned within the proximal sleeve of the balloon in order to inflate the balloon.

11. The apparatus as set forth in claim 10 wherein the guide wire and fluid lumen of the catheter are coaxial.

12. The apparatus as set forth in claim 10 wherein the guide wire and fluid lumen of the catheter are in a side-by-side arrangement.

13. A method of dilating and imaging a stenosis of a blood vessel, the method utilizing a single dilating apparatus having an inflatable balloon secured to a distal end of a catheter for receiving pressurized fluid from the catheter, the apparatus including an imaging device positioned behind an expandable portion of the balloon so as to enable the balloon to achieve a low profile having a diameter smaller than that of the imaging device and enabling the deflated balloon to enter a stenosis having a smaller diameter than that of the imaging device, the method comprising the steps of:
inserting a guide wire into a blood vessel of a patient to a position that extends through the stenosis;
inserting the inflatable balloon into the vessel along the guide wire that passes through a lumen of the apparatus until the balloon is positioned within the stenosis;
inflating the balloon with pressurized fluid communicated via the catheter so as to dilate the stenosis;
deflating the balloon by removing the pressurized fluid from the balloon; and
advancing the imaging device into the stenosis by further inserting the catheter into the blood vessel in order to examine the stenosis.

14. A method of simultaneously dilating and imaging a stenosis of a blood vessel, the method utilizing a single dilating apparatus having an inflatable balloon at a distal end of a catheter for receiving pressurized fluid from the catheter and an imaging device slidably mounted on a tubing within the balloon, the method comprising the steps of:
inserting a guide wire into a blood vessel of a patient to a position that extends through the stenosis;
positioning the imaging device within a proximal sleeve of the balloon;
inserting the balloon in a deflated condition into the vessel along the guide wire that passes through the tubing until the balloon is positioned within the stenosis;
inflating the balloon with pressurized fluid communicated via the catheter so as to dilate the stenosis; and
sliding the imaging device along the tubing and into an expandable portion of the inflated balloon using a push wire in order to examine portions of the stenosis being dilated, wherein the push wire is attached to the imaging device and is controlled from a proximal end of the catheter.

15. The method as set forth in claim 14, further comprising the steps of:
sliding the imaging device back into the proximal end of the balloon;
deflating the balloon by removing the pressurized fluid from the balloon; and
advancing the imaging device into the stenosis by further inserting the catheter into the blood vessel in order to examine the stenosis after it has been dilated by the balloon.

* * * * *